US00PP10524P

United States Patent [19]

Jessel, Jr.

[11] Patent Number: Plant 10,524

[45] Date of Patent: Jul. 28, 1998

[54] CARNATION PLANT NAMED 'CFPC PEACH MAJESTIC'

[75] Inventor: Walter H. Jessel, Jr., Gonzales, Calif.

[73] Assignee: California Florida Plant Co., L.P., Salinas, Calif.

[21] Appl. No.: 711,035

[22] Filed: Sep. 10, 1996

[51] Int. Cl.[6] ..... A01H 5/00

[52] U.S. Cl. ..... Plt./70.5

[58] Field of Search ..... Plt./70.2, 70.5, Plt./70.6

*Primary Examiner*—Howard J. Locker

*Attorney, Agent, or Firm*—Christie, Parker & Hale, LLP

[57] ABSTRACT

A new plant variety of carnation plant producing sprays of peach pink flowers.

1 Drawing Sheet

SUMMARY OF THE INVENTION

The present invention relates to a new and distinct variety of carnation plant which was discovered as a sport in a controlled planting of the cultivar 'CFPC Majestic,' U.S. Plant Pat. No. 8,104. The varietal denomination of this new carnation is 'CFPC Peach Majestic'.

Among the novel combination of characteristics possessed by the new variety which distinguishes it from its parent are superior resistance to airborne diseases such as *F. oxysporum*, strains 1 and 2, and *F. graminearum*, and sprays of small-to-medium peach pink flowers.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (RHSCC). The terminology used in color description herein refers to plate numbers in the aforementioned color chart. Phenotypic expression and color descriptions may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Peach Majestic'.

Classification:

*Botanical.*—*Dianthus caryophyllus.*

*Commercial.*—Carnation, spray type.

Parentage: Sport of 'CFPC Majestic.'

1. Plant:
   - *Height.*—Pinched plants are about 39 inches tall (first flowering).

- *Growing habit.*—Herbaceous, semi-upright.
   - *Blooming habit.*—As a spray.
   - *Blooming season.*—Year round.
   - *Rooting time.*—About 17 days.
   - *Mutation prone.*—No.
   - *Disease resistance.*—Very good.
   - *Temperature tolerance.*—Wide range.
   - *Breaking action.*—Very good, about 8 to 9 lateral shoots per plant.
2. Foliage:
   - *Color.*—Upper side: Near 137A. Lower side: Near 137A.
   - *Size.*—About 7¼ inches long, about ¼ inches wide.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem color.*—Near 137C.
3. Bud:
   - *Shape.*—Oval.
   - *Color.*—Near 137C.
   - *Length.*—About 1 inch.
   - *Diameter.*—About ½ inch.
4. Calyx:
   - *Number of sepals.*—About 6.
   - *Length.*—About ¼ inch.
   - *Width.*—About ¼ inch.
   - *Color.*—Outside — Near 137C. Inside — Near 145C.
5. Bloom:
   - *Shape.*—Round.
   - *Size.*—Diameter average: About 1½ inches. Depth average: About ¾ inch.
   - *Borne.*—As a spray, terminal sprays of about 7 to 8 blooms; stem length approximately 39 inches.
   - *Color.*—General tonality: Peach pink. Upper side: Near 49C. Lower side: Near 49B. Center: Near 49C. Outer petals: Near 49C.
   - *Keeping quality.*—Very good, entire flower flush per stem lasts about 2 to 3 weeks.
   - *Fragrance.*—Slight.
6. Petals:
   - *Number.*—About 22.
   - *Outer most petals.*—Length; About 1¾ inches. Width: About ⅝ inch.
   - *Central petals.*—Length: About 1½ inches. Width: About ¼ inch.
   - *Texture.*—Smooth.

*Form.*—Fan shaped.

*Apperance.*—Shiny, petal margin is smooth.

7. Reproductive organs:

*Stamens.*—About 6.

*Anthers.*—About ⅛ inch, near 19D.

*Filaments.*—About ¾ inch, whiter than 155D.

*Pistil.*—Number About 1. Color: Whiter than 155D. Length: About 1 inch.

*Stigma.*—Number: About 2. Color: Whiter than 155D.

*Ovary.*—Shape: Conical. Color: Base— whiter than 155D. Body— whiter than 155D. Apex— Near 143C.

*Fertility.*—Female: Poor. Male: Fair.

I claim:

1. A new and distinct variety of carnation plant substantially as shown and described.

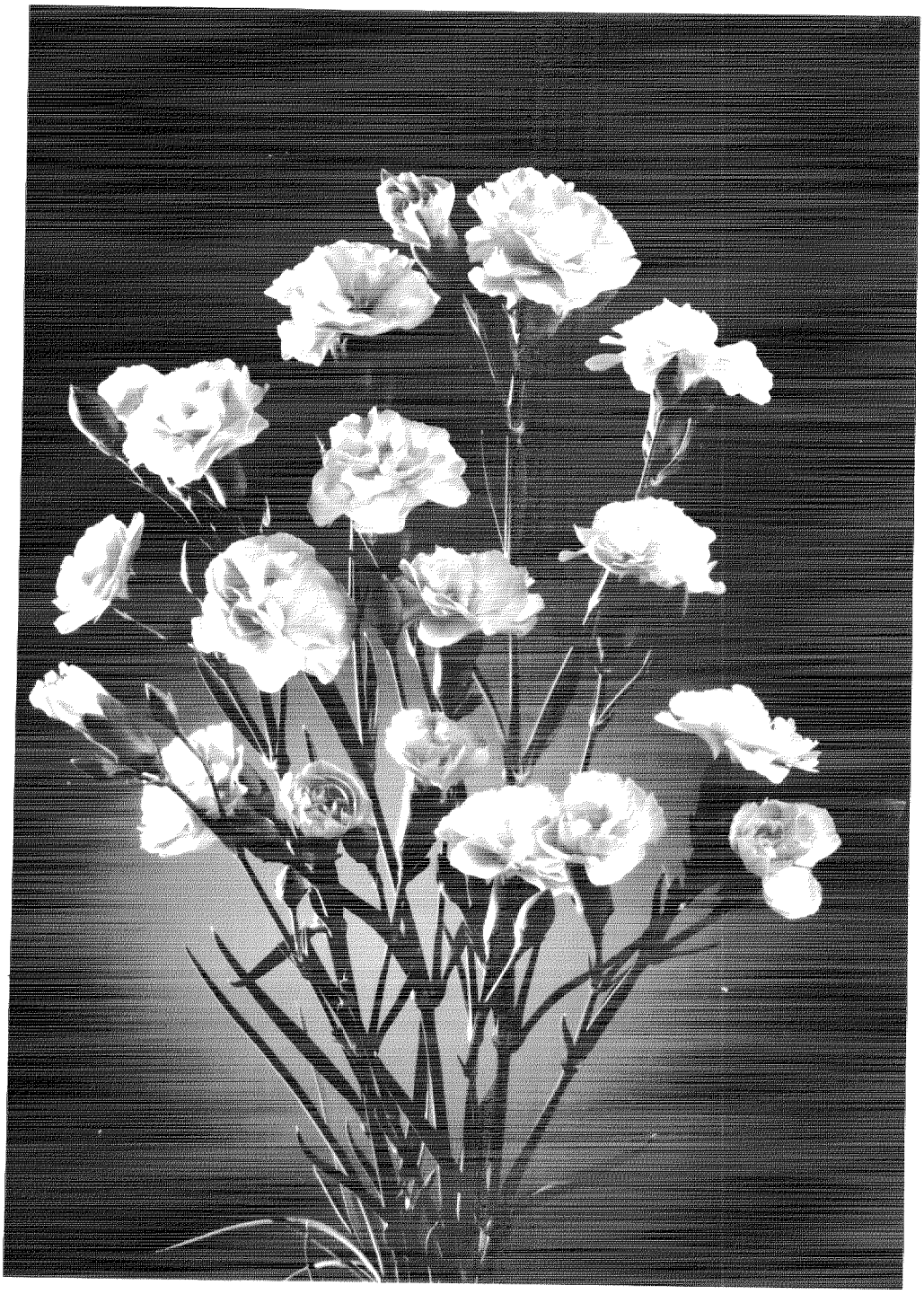

* * * * *